US012029500B2

(12) United States Patent
Van Der Zaag et al.

(10) Patent No.: US 12,029,500 B2
(45) Date of Patent: Jul. 9, 2024

(54) SYSTEM FOR AFFECTING A SUBJECT

(71) Applicant: KONINKLIJKE PHILIPS N.V., Eindhoven (NL)

(72) Inventors: Pieter Jan Van Der Zaag, Waalre (NL); Christiaan Varekamp, Veldhoven (NL); Bernardus Hendrikus Wilhelmus Hendriks, Eindhoven (NL); John Pedersen, Maple Grove, MN (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 116 days.

(21) Appl. No.: 17/053,789

(22) PCT Filed: May 5, 2019

(86) PCT No.: PCT/EP2019/061472
§ 371 (c)(1),
(2) Date: Nov. 8, 2020

(87) PCT Pub. No.: WO2019/215056
PCT Pub. Date: Nov. 14, 2019

(65) Prior Publication Data
US 2021/0259780 A1    Aug. 26, 2021

(30) Foreign Application Priority Data
May 7, 2018   (EP) .................................. 18171082

(51) Int. Cl.
*A61B 34/20*    (2016.01)
*A61B 34/30*    (2016.01)
*A61B 90/00*    (2016.01)

(52) U.S. Cl.
CPC .............. *A61B 34/20* (2016.02); *A61B 34/30* (2016.02); *A61B 90/37* (2016.02);
(Continued)

(58) Field of Classification Search
CPC ......... A61B 34/20; A61B 34/30; A61B 90/37; A61B 2034/2051; A61B 2090/374;
(Continued)

(56) References Cited

U.S. PATENT DOCUMENTS

| 6,419,484 B1 | 7/2002 | DaSilva et al. | |
| 2003/0181800 A1* | 9/2003 | Bonutti .................. | A61B 17/14 600/407 |

(Continued)

FOREIGN PATENT DOCUMENTS

| EP | 2772199 A1 | 9/2014 |
| JP | 11267133 A | 10/1999 |

(Continued)

OTHER PUBLICATIONS

Breyer et al: "Ultrasonically Marked Catheter—A Method for Positive Echographic Catheter Position Identification"; Med & Biol Eng. & Comput. 1984, 22, pp. 268-271.

(Continued)

*Primary Examiner* — Colin T. Sakamoto
*Assistant Examiner* — Tommy T Ly (57) ABSTRACT

The invention refers to a system (100) for affecting a subject and a method for operating the system comprising a medical device like a biopsy gun (130) set in a first state in which it is not able to affect the subject based on a trigger signal or in a second state in which it is able to affect the subject based on the trigger signal, wherein the state is set based on a provided location of the medical device, i.e., for instance, is set based on the distance of the medical device to a target region. The location of the medical device is provided by a location providing unit (140) comprising, for instance, an imaging unit like an ultrasound system (142). Thus, unin- (Continued)

tended, possible dangerous injuries of the patient are prevented and the safety of the patient during the interventional procedure is increased.

20 Claims, 2 Drawing Sheets

(52) U.S. Cl.
CPC . *A61B 2034/2051* (2016.02); *A61B 2090/374* (2016.02); *A61B 2090/3762* (2016.02); *A61B 2090/378* (2016.02)

(58) Field of Classification Search
CPC ...... A61B 2090/3762; A61B 2090/378; A61B 2010/0208; A61B 2034/2055; A61B 2034/2065; A61B 2090/376; A61B 10/0233; A61B 10/0275; A61B 17/3403; A61B 2017/3413; A61B 8/0841; A61B 8/12; A61B 2010/045; A61B 34/32; A61B 2017/00017; A61N 5/1001; G06V 2201/034
See application file for complete search history.

(56) References Cited

U.S. PATENT DOCUMENTS

| | | | |
|---|---|---|---|
| 2007/0073136 A1* | 3/2007 | Metzger | A61B 34/20 600/407 |
| 2009/0155735 A1 | 6/2009 | Hauger | |
| 2012/0197110 A1* | 8/2012 | Hartmann | H01F 5/00 600/424 |
| 2013/0310680 A1 | 11/2013 | Werahera et al. | |
| 2013/0338477 A1 | 12/2013 | Glossop et al. | |
| 2013/0345718 A1 | 12/2013 | Crawford et al. | |
| 2014/0228632 A1 | 8/2014 | Sholev et al. | |
| 2016/0256273 A1* | 9/2016 | Glazier | A61F 2/958 |
| 2016/0302871 A1* | 10/2016 | Gregerson | A61B 46/10 |
| 2017/0196654 A1* | 7/2017 | Toyoda | A61B 17/1673 |
| 2017/0202636 A1 | 7/2017 | Huang et al. | |
| 2017/0311933 A1* | 11/2017 | Tanghal | A61B 10/0275 |
| 2017/0333033 A1* | 11/2017 | Valentine | A61B 17/068 |
| 2017/0348061 A1* | 12/2017 | Joshi | A61B 34/25 |
| 2018/0168780 A1* | 6/2018 | Kopelman | G16H 30/40 |
| 2018/0289432 A1* | 10/2018 | Kostrzewski | A61B 34/30 |
| 2019/0192138 A1* | 6/2019 | Shelton, IV | A61F 5/0036 |
| 2019/0201110 A1* | 7/2019 | Kuenen | G01S 15/8993 |
| 2020/0038121 A1* | 2/2020 | Yang | A61B 90/50 |
| 2021/0059775 A1* | 3/2021 | Peine | A61B 34/20 |

FOREIGN PATENT DOCUMENTS

| | | | | |
|---|---|---|---|---|
| JP | 2003126093 A | 5/2003 | | |
| JP | 2004351230 A | 12/2004 | | |
| JP | 2016505326 A | 2/2016 | | |
| WO | 2004014246 A1 | 2/2004 | | |
| WO | 2007005976 A1 | 1/2007 | | |
| WO | WO-2008030264 A1 * | 3/2008 | ............ | A61B 34/20 |
| WO | 2009153723 A1 | 12/2009 | | |
| WO | 2016075061 A1 | 5/2016 | | |
| WO | 2016187664 A1 | 12/2016 | | |
| WO | 2017017556 A1 | 2/2017 | | |
| WO | 2017042650 A2 | 3/2017 | | |
| WO | 2017109201 A1 | 6/2017 | | |
| WO | 2017194563 A1 | 11/2017 | | |
| WO | 2017203231 A1 | 11/2017 | | |
| WO | 2018060404 A1 | 4/2018 | | |
| WO | 2019092168 A1 | 5/2019 | | |
| WO | 2019105866 A1 | 6/2019 | | |
| WO | 2019110431 A1 | 6/2019 | | |

OTHER PUBLICATIONS

Guo et al: "Active Ultrasound Pattern Injection System (AUSPIS) for Interventional Tool Guidance"; PLoS ONE Oct. 2014, vol. 9(10):e104262.
PCT/EP2019/061472 ISR & WO, Aug. 19, 2019, 14 Pages.
Rovetta et al: "Execution of Robot-Assisted Biopsies Within the Clinical Context"; Journal of Image Guided Surgery, 1:5, pp. 280-287, 1995.
Verhaegh et al: "Selection of Personalized Patient Therapy Through the Use of Knowledge-Based Computational Modelsthat Identify Tumor-Driving Signal Transduction Pathways"; Cancer Res: 74(11), Jun. 1, 2014, pp. 2936-2945.

* cited by examiner

SYSTEM FOR AFFECTING A SUBJECT

CROSS-REFERENCE TO PRIOR APPLICATIONS

This application is the U.S. National Phase application under 35 U.S.C. § 371 of International Application No. PCT/EP2019/061472, filed on May 5, 2019, which claims the benefit of European Patent Application No. 18171082.3, filed on May 7, 2018. These applications are hereby incorporated by reference herein.

FIELD OF THE INVENTION

The invention relates to a system for affecting a subject, a device control unit for controlling a medical device for affecting a subject, and a method and a computer program for operating the system.

BACKGROUND OF THE INVENTION

Many medical devices that can affect the body of a patient, such as a biopsy gun for taking a biopsy, are operated using a trigger signal that determines when the body should be affected, for instance, when the biopsy should be taken. The trigger signal will be provided either by a human practitioner, for instance, a physician navigating the medical device, or by a robot system navigating the medical device. Although the operating of the medical device is always supervised, for instance, by using image guidance, it cannot be ruled out that the trigger signal is provided by accident at the wrong place or time. Such an accidentally provided trigger signal can lead to unintended and unnecessary injuries of the patient that may cause severe complications during the interventional proceeding.

SUMMARY OF THE INVENTION

It is an object of the present invention to provide a system for affecting a subject, a device control unit for controlling a medical device for affecting a subject, and a method and a computer program for operating the system which allow for an improved safety of a patient during an interventional procedure.

In a first aspect of the present invention a system for affecting a subject is presented, wherein the system comprises:
  a medical device configured to affect the subject, wherein the medical device is configured to be in a first state or in a second state, wherein in the first state the medical device is not able to affect the subject in response to a provided trigger signal, wherein in the second state the medical device is able to affect the subject in response to the trigger signal,
  a device location providing unit for providing a location of the medical device, and
  a device control unit for controlling the medical device, wherein the device control unit is configured to set the medical device to the first state or the second state based on the provided location of the medical device.

Since the device control unit is configured to set the medical device to the first state or the second state based on the provided location of the medical device, wherein in the first state the medical device is not able to affect the subject in response to a provided trigger signal, and in the second state the medical device is able to affect the subject in response to the trigger signal, the medical device will only respond to the trigger signal in a region where it is intended to affect the subject or where it is safe for the medical device to affect the subject, whereas a trigger signal provided accidentally, when the medical device is in an area where it is not intended or would not be safe to affect the subject, will not cause a response of the medical device, i.e. the medical device will not affect the subject in this case. Thus, unintended, possible dangerous injuries of the patient are prevented and the safety of the patient during the interventional procedure is increased. The first state of the medical device can therefore be regarded as a safety state, i.e., a state in which the medical device will not respond to a provided trigger signal by affecting the subject.

In a preferred embodiment the device control unit is configured to set the medical device to the first state, i.e. the safety state, if the medical device determines based on the provided location of the medical device that the medical device is in a location in which it would not be safe to affect the subject, and to set the medical device in the second state if the medical device determines based on the provided location of the medical device that the medical device is in a location in which it would be safe to affect the subject. The subject is affected by the medical device when the medical device physically influences the subject, i.e. leads to a difference in the physical state of the subject compared with the state of the subject before the medical device affected it. Preferably, a movement of the medical device, for instance, the navigation of the medical device, from one location to another location, is not affected by the first or the second state of the medical device. Moreover, the medical device can be configured to comprise more than one second state, wherein in each second state the medical device is able to affect the subject differently in response to the trigger signal. For instance, if the medical device is a biopsy gun, a first second state can refer to taking a biopsy in a depth of 10 mm and a second state allows to take a biopsy in a depth of 15 or 20 mm when the trigger signal is provided.

The device location providing unit provides the location of the medical device, wherein the location of the medical device can be provided, for instance, by a localization system like an x-ray localization system, an electromagnetic localization system, an optical shape sensing localization system such as the one disclosed in US 2013/0308138 A1, et cetera. The location can be provided as coordinates in a predetermined coordinate system, or can be provided as difference to a predetermined area. Preferably, the provided location of the medical device refers to a tip of the medical device. For instance, if the medical device is a biopsy gun, the provided location can refer to a tip of a needle of the biopsy gun. In other embodiments the provided location can refer to other relevant parts of the medical device, i.e. the parts of the device with which the patient can be affected.

The device control unit can be realized, for instance, as dedicated hardware unit or as software unit that, when executed on a processor, allows for the controlling of the medical device. Preferably, the device control unit is located in the medical device, for instance, in a handle of the medical device. Alternatively, the device control unit can be located in the device location providing unit.

In an embodiment, the location providing unit can also be adapted to provide an orientation of the device and the device control unit can be adapted to set the medical device to the first state or the second state further based on the provided orientation of the medical device.

In an embodiment the system further comprises a target region providing unit for providing a target region in the subject, wherein the target region is a region in which the medical device should affect the subject, wherein the device control unit is configured to set the medical device to the first state if the provided location of the medical device is outside the target region and to the second state if the provided location of the medical device is within the target region. The target region providing unit can be adapted to provide, for instance, predetermined locations within the subject as the target region, or can provide a 2D or 3D boundary of an area within the subject as the target region. The target region can be determined based on preoperative medical images of the subject, saved in a hardware or software component and then provided during the interventional procedure. Alternatively, the target region can be determined based on images taken during the interventional procedure and provided in real-time. Moreover, the target region providing unit can further provide an interventional plan comprising a plurality of regions in which the medical device should affect the subject, wherein during the interventional procedure the target region providing unit provides the region that should be affected next by the medical device as the target region. The target region providing unit and the localization providing unit can be registered to each other, i.e. to a common coordinate system, before an interventional procedure using one of the known registration techniques, or the location of the target region can be determined in an image in which also the medical device is visible such that the coordinates of the target region and the medical device are known in the same coordinate system. Moreover, the target region providing unit can further be adapted to provide a target orientation of the medical device and the device control unit is adapted to set the medical device into the second state if the medical device is not only in the target region but also in the target orientation of the medical device. In particular, the device control unit can further be adapted to check in addition to the location of the interventional device also an orientation of the device, wherein if the interventional device is within a target region and also within a predetermined target orientation, the interventional device is set to the second state. Preferably, the target region providing unit can also be adapted to provide a danger region, for instance, a "danger zone", in which the medical device should not affect the subject. The device control unit can then be adapted to set the medical device from the second state into the first state, if it is determined that the medical device enters the danger region. Preferably, in a danger region a user of the medical device, for instance, a surgeon, cannot override the setting of the medical device, for instance, by manually setting the medical device into the second state.

Preferably, the medical device is configured to comprise a plurality of second states, wherein in each second state the medical device is able to affect the subject differently in response to the trigger signal, wherein the system comprises a second state determination unit for determining based on characteristics of the target region a second state of the plurality of second states, and wherein the device control unit is configured to set the medical device to the determined second state if the provided location of the medical device is within the target region. The characteristics of the target region can comprise tissue characteristics of the tissue within the target region, like the stiffness or viscosity of the tissue, or can comprise characteristics of the tissue structure of the target region, like presence and location of large or small blood vessels, the amount of expected cancerous tissue in the region, or the extent of the target region. The second state determination unit can be adapted to receive the characteristics of the target region, for instance, from a data storage, in which tissue characteristics of the target region are stored. Alternatively, the characteristics of the target region can be provided by a medical practitioner, or the characteristics of the target region can be determined by the second state determination unit, for instance, based on a provided medical image of the target region. Moreover, the characteristics of the target region can be determined by the medical device, for instance by using a measuring unit provided in the medical device, wherein the measuring unit is adapted to measure the characteristics of tissue. The measuring unit can be, for instance, a photonic measurement device. Preferably, the second state determination unit is adapted to determine the effect of affecting the subject using the medical device in all of the second states based on the characteristics of the target region and to determine the second state for the target region from among the plurality of second states based on this effect. In particular, the second state determination unit is adapted to determine which second state safely affects the patient in the target region based on the determined effect.

In an embodiment the first state comprises a first stage and a second stage, wherein in the first stage the medical device is not able to change its physical state and in the second stage the medical device is able to change its physical state based on a change signal, wherein the device control unit is further configured to set the medical device to the first stage of the first state or to the second stage of the first state based on the provided location of the medical device. The change of the physical state refers to a change in the physical characteristics of the device from one state to the other. For instance, the physical characteristics can correspond to a structure of the device, an appearance of the device, a volume of the device, or a material characteristic of the device. In the changed physical state the medical device is not able to affect the subject as long as the device is in the first state. Preferably, the device control unit is further configured to first set the medical device to the second stage of the first state before setting the medical device to the second state. More preferably, the device control unit is configured to set the medical device into the second stage of the first state, if the device control unit determined that the medical device is in the target region, and to set the medical device into the second state only after checking that the medical device is still in the target region. In this embodiment the device control unit can be adapted to set the medical device in the second state upon request of the user of the medical device after checking that the medical device is still in the target region. Additionally or alternatively, the target region can comprise a target sub-region, wherein the device control unit can be adapted to set the medical device from the second stage of the first state into the second state, if the device control unit determines that the medical device is in the target sub-region.

In this embodiment the medical device is preferably a stent or balloon applicator comprising a stent or balloon, wherein in the first stage of the first state the stent or balloon applicator is not able to change its physical state by changing the physical state of the stent or balloon and in the second stage of the first state the stent or balloon applicator is able to change its physical state by changing the physical state of the stent or balloon, and wherein in the second state the stent or balloon applicator is able to apply the stent or balloon to the patient based on the trigger signal. Preferably, in the second stage the stent or balloon applicator is able to change the physical state of the stent or balloon from a closed state to a partly opened state, in which the stent or balloon only unfolds partly. Moreover, the application of the stent or balloon preferably comprises opening, i.e. unfolding, the stent or balloon completely from the partly opened state, wherein in the completely opened state the stent or balloon affects a subject, for instance, by opening a blood vessel or applying a drug to the walls of a blood vessel.

In an embodiment the device location providing unit comprises an image providing unit for providing an image of the medical device, and a device location determination unit for determining the location of the medical device in the provided image as the location. The image providing unit can be, for instance, an ultrasound imaging system, a CT system, an MRI system or an x-ray imaging system. The medical device is preferably configured to provide a good detectability in the medical image of the respective image providing unit, for instance, by providing at least one marker attached to the medical device visible in the provided image. Preferably, the image providing unit provides the image of the medical device in real-time, i.e. continuously during the interventional procedure.

The device location determination unit is preferably adapted to automatically detect the medical device in the provided image and to determine the location of the medical device based on the detected medical device in the provided image. As location of the medical device, for instance, a tip of the medical device can be provided. Preferably, the device location determination unit is adapted to continuously track the location of the medical device in the provided image and to provide the current location of the medical device in the provided image as the location.

It is preferred that the system further comprises a target region providing unit for providing a target region in the provided image, wherein the target region is a region in which the medical device should affect the subject and wherein the device control unit is configured to set the medical device to the first state if the provided location of the medical device is outside the target region, and to the second state if the provided location of the medical device is within the target region. The target region providing unit can be adapted to register a predetermined location of the target region with the provided image such that the target region is shown in the provided image. In a preferred embodiment the target region providing unit is adapted to highlight the target region in the provided image, for instance, using colors, and to display the highlighted target region in the provided image to a user. In this embodiment the user has the opportunity to review the target region and, if necessary, correct a location or a boundary of the target region. In another preferred embodiment the target region providing unit is adapted to determine the target region based on the provided image. The target region providing unit can be adapted to segment the provided image using known segmentation techniques and to determine tissue segments of the provided image that should be affected by the medical device as target region.

Preferably, the system further comprises a communication signal providing unit for providing a communication signal from the device location providing unit to the device control unit, and/or from the device control unit to the device location providing unit, wherein the communication signal from the device location providing unit to the device control unit comprises the location of the medical device. The communication signal providing unit can provide the communication signal from the device location providing unit to the device control unit and/or the communication signal from the device control unit to the device location providing unit via a wired or wireless data connection. Moreover, the communication signal providing unit can be, for instance, a WLAN providing unit, a LAN providing unit, a Bluetooth providing unit, an infrared providing unit, et cetera. Moreover, the communication signal from the device location providing unit to the device control unit can further comprise the location of the target region and/or the provided image. Furthermore, in an embodiment the communication signal from device location providing unit to the device control unit can comprise a signal prompting the device control unit to change the state of the medical device, and/or the trigger signal for triggering the medical device to affect the subject. In an embodiment the medical device comprises further a sensor for measuring a characteristic of the surrounding of the medical device, for instance, for measuring temperature, pressure, pH, etc., wherein the communication signal from the device location providing unit to the device control unit can comprise a signal prompting the medical device to take a measurement using the sensor. The communication signal from the device control unit to the device location providing unit can comprise a number of a biopsy taken by the medical device, a signal being indicative of the current state of the medical device, a confirmation that the subject has been affected due to the trigger signal and/or information from the sensor attached to the medical device for measuring characteristics of the surrounding of the medical device like temperature, pressure, etc.

Further preferably the communication signal from the device control unit to the device location providing unit comprises a device signal, wherein the device signal is indicative of the current state of the medical device, wherein the device location providing unit comprises an image providing unit and the image providing unit provides an image of the medical device based on the state signal. Preferably, the image providing unit is adapted to provide a first image comprising first imaging settings if the device signal indicates that the medical device is in the first state and a second image with second imaging settings if the device signal indicates that the medical device is in the second state. Preferably, the first images are used during the navigation of a medical device to the target region such that the first imaging settings of the first image are specifically adapted for this purpose, whereas, when the target region is reached, the second image comprising the second imaging settings is used, wherein the second imaging settings are specifically adapted to allow the determination of an optimal site for affecting the subject with the medical device. Preferably the first imaging settings of the first image comprise a lower spatial or temporal resolution than the second imaging settings of the second image. In an embodiment the image providing unit is an x-ray system, wherein the first imaging setting provides less radiation load to the patient than the second imaging setting. In an alternative embodiment the image providing unit is an ultrasound system, wherein the first imaging setting refers to settings for acquiring a 2D ultrasound image and the second imaging settings refer to settings for acquiring a 3D ultrasound image.

In a preferred embodiment the image providing unit is an ultrasound device or an x-ray device and the medical device is a biopsy gun or a brachytherapy applicator, wherein the first state is an unarmed state and the second state is an armed state of the biopsy gun or the applicator, respectively. The x-ray device can be any device using x-rays for providing a medical image, for instance, a CT system, an x-ray camera, an angiography system, et cetera. If the medical device is a biopsy gun, the biopsy gun affects the subject by taking a biopsy at the predetermined location. If the medical device is a brachytherapy applicator, the brachytherapy applicator affects the subject by placing a radioactive seed at a predetermined location in the body of the subject. The first state, i.e. the armed state, is a state in which the trigger signal, if applied to the biopsy gun or the brachytherapy applicator, will not cause the taking of the biopsy or the setting of a radioactive seed, respectively. The second state, i.e. the armed state, is the state in which the providing of the trigger signal causes the biopsy gun or the brachytherapy applicator to take a biopsy or to place the radioactive seed, respectively.

In an embodiment the medical device is an electrosurgical device, wherein the first state is a resting state and the second state is an active state of the electrosurgical device. The resting state refers to a state in which the electrosurgical device cannot be used for affecting the patient, preferably is not supplied with electrical power. The active state is a state in which the electrosurgical device can affect the patient based on a trigger signal of the user. Preferably, in the active state the electrosurgical device is supplied with electrical power such that a trigger signal allows the electrosurgical device to start working. In a preferred embodiment the electrosurgical device is an electrosurgical knife.

In an embodiment the medical device is a medical drill, preferably adapted for spinal surgery, wherein the first state can refer to a state in which the medical drill is not able to rotate the drill bit, and the second state to a state in which it is able to rotate the drill bit.

In an embodiment the medical device is an interventional device, preferably adapted for taking a lung biopsy through entering the bronchial paths of the lung, wherein in the first state the interventional device is not able to take the biopsy, for instance, is not able to shoot a biopsy needle into tissue, and in the second state it is able to take the biopsy, for instance, by shooting the needle into tissue.

Moreover, the medical device can also be an injection needle adapted for being used in an image guided procedure for injecting a regional anesthetic, an arterial or atherectomy device, a thrombectomy device, a laser ablation device, or a cryotherapy device.

In an embodiment, the device control unit is adapted to provide an alarm if the medical device is set from the first state to the second state and/or if the medical device is set from the second state to the first state. Moreover, the device control unit can be adapted to provide an alarm, if the device control unit determines, based on the provided location of the medical device and based on the target region, that the medical device has moved from a location inside the target region to a location outside the target region. The alarm can be an acoustical and/or visual signal.

In an embodiment the system comprises a medical robot, wherein the medical robot comprises a medical device navigation unit configured to navigate the medical device, and a trigger signal providing unit for providing the trigger signal to the medical device, wherein the trigger signal is provided when the medical robot determines based on the provided location that the medical device is at a predetermined location. The medical robot can be a full automated or half automated robotic system.

In a further aspect of the present invention a device control unit for controlling a medical device for affecting a subject is presented, wherein the medical device is configured to be in a first state or in a second state, wherein in the first state the medical device is not able to affect the subject in response to a provided trigger signal, wherein in the second state the medical device is able to affect the subject in response to the trigger signal, wherein the device control unit is configured to set the medical device to the first state or the second state based on a provided location of the medical device.

In a further aspect of the present invention, a method for operating the system as defined above is presented, wherein the method comprises:
providing the location of the medical device by a device location providing unit,
setting the first state or the second state of the medical device based on the provided location of the medical device by a device control unit.

Preferably, the method further comprises providing a trigger signal, wherein the subject is not affected by the medical device if the medical device is in the first state, and the subject is affected by the medical device if the medical device is in the second state.

In a further aspect of the present invention, a computer program for operating the system as defined in claim 1 is presented, wherein the computer program comprises program code means for causing the system to carry out the steps of the method as defined in claim 13 when the computer program is run on a computer controlling the system.

It shall be understood that the system for affecting a subject of claim 1, the device control unit for controlling a medical device for affecting the subject of claim 12, the method for operating a system of claim 14, and the computer program of claim 15, have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

In the following drawings.

DETAILED DESCRIPTION OF EMBODIMENTS

Figure 1:
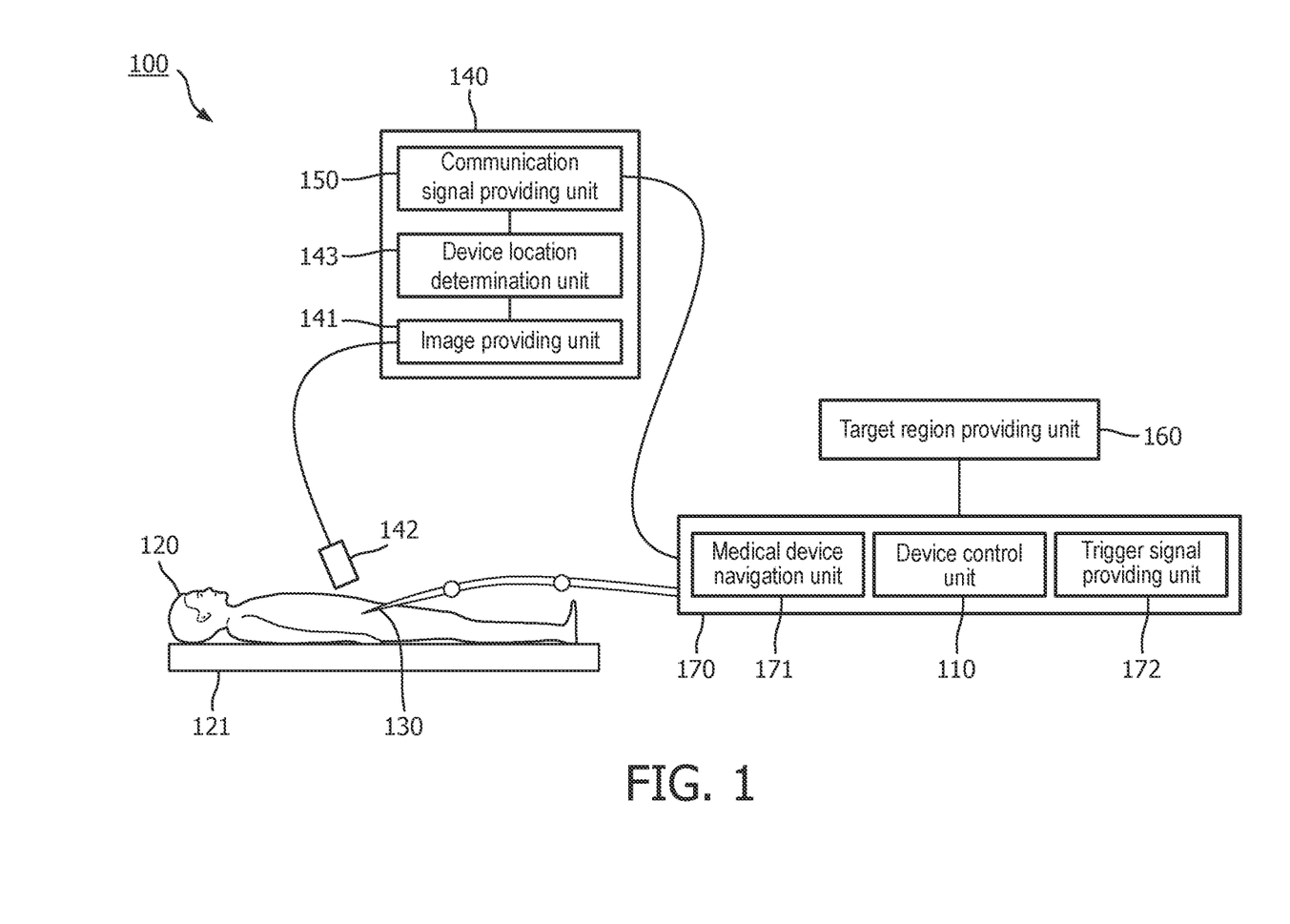
FIG. 1 shows schematically and exemplarily an embodiment of a system for affecting a subject.

FIG. 1 shows schematically and exemplarily an embodiment of a system for affecting a subject. In this embodiment the system 100 is adapted to take a biopsy within a person 120 lying on a support means 121 like a patient table. The system 100 comprises a biopsy gun 130 being a medical device configured to affect the subject 120 by taking a biopsy, in particular, by taking a biopsy of a tumor within the subject 120. For taking the biopsy the biopsy gun comprises a biopsy needle, wherein due to the provision of a trigger signal the biopsy needle is extended into tissue of the patient 120 to take the biopsy. The biopsy gun 130 is configured to be in a first state being an unarmed state, i.e. a safety state, in which a trigger signal does not result in the taking of a biopsy or in a second state being an armed state in which the provision of a trigger signal causes the taking of a biopsy. In the unarmed state the biopsy needle of the biopsy gun 130 is mechanically or electrically locked such that no extension of the biopsy needle is possible. In the armed state the biopsy needle of the biopsy gun 130 is mechanically or electrically unlocked such that the biopsy needle can be extended into the tissue of the patient when a trigger signal is provided.

In this embodiment, the biopsy gun 130 is navigated by a medical robot 170 comprising a medical device navigation unit 171 for navigating the biopsy gun 130, a device control unit 110 for controlling the biopsy gun 130 and a trigger signal providing unit 172 for providing a trigger signal to the biopsy gun 130. The medical device navigation unit 171 uses means of the medical robot 170, for instance, a mechanical robot arm, to navigate the biopsy gun 130 to a target area within the body of the patient. For navigating the biopsy gun 130 the medical device navigation unit 171 can use a predetermined path to the target region or any other know automatic navigation technique. The device control unit 110 is configured to set the biopsy gun 130 to the unarmed state or the armed state by providing a signal indicative of the required state to the biopsy gun 130 causing the biopsy gun 130 to set the indicated state. The trigger signal providing unit 172 is adapted to provide the trigger signal to the biopsy gun 130 that causes the biopsy gun 130 to extend the biopsy needle and take the biopsy.

The system 100 further comprises a device location providing unit 140 for providing a location of the medical device within the subject 120. The device location providing unit 140 comprises an ultrasound device 142 that communicates ultrasound data to an image providing unit 141, wherein the image providing unit 141 provides an ultrasound image comprising at least a part of the biopsy gun 130 within the subject 120 based on the ultrasound data from the ultrasound device 142. The ultrasound image provided by the image providing unit 141 is, for instance, a 2D or a 3D ultrasound image. The device location providing unit 140 further comprises a device location determination unit 143 for determining the location of the biopsy gun 130 in the ultrasound image. In this embodiment, the device location determination unit 143 is adapted to automatically recognize the biopsy gun 130 within the provided ultrasound image, wherein a tip of a needle within the biopsy gun 130 is determined as location of the biopsy gun 130 within the ultrasound image. In this embodiment the device location providing unit 140 further comprises a communication signal providing unit 150 for providing a communication signal comprising the location of the biopsy gun 130 to the medical robot 170.

The system 100 further comprises a target region providing unit 160 for providing a target region, such as a tumor, for which a biopsy should be taken, to the medical robot 170. The target region providing unit 160 can provide the target region based on a predetermined target location, wherein the predetermined target location is the location at which the biopsy should be taken. In particular, the target region providing unit 160 provides a safety margin around the target location, wherein the safety margin, together with the target location, forms the target region.

In this embodiment the target region providing unit 160, the device location providing unit 140 and the medical robot 170 are registered to each other, i.e. locations provided by these units are provided in the same coordinate system. The registration can be performed before the start of the interventional procedure using an already known registration technique, for instance, by marking the medical device in a preoperative image provided by the image providing unit 141 showing the medical device and/or by using markers in a preoperative image and an intraoperative image, like the ultrasound image, at known locations, also a calibration or registration phantom can be used.

Based on the location of the provided target region and the location of the biopsy gun 130 in the provided image the device control unit 110 of the medical robot 170 sets the biopsy gun 130 to the first state being the unarmed state if the location of the biopsy gun 130 is outside of the target region, and to the second state being the armed state if the biopsy gun 130 is within the target region. If the medical robot 170 further determines that the biopsy gun 130 is located within the target region in a place optimal for taking the biopsy, in particular at the target location, the trigger signal providing unit 172 provides the trigger signal to the biopsy gun 130, wherein based on the trigger signal the biopsy gun 130 takes the biopsy.

Although in above described embodiments the medical device, for instance, the biopsy gun, is navigated and triggered by a medical robot, in another embodiment the medical device is navigated and triggered by a medical practitioner. In such an embodiment, the device control unit can be provided in the medical device, for instance, in a handle of the medical device or in a component connected to the medical device. The location providing unit then directly provides the location of the medical device to the device control unit in the medical device. Further, also the target region providing unit directly provides the target region to the device control unit in the medical device. The device control unit in this embodiment comprises means for determining if the medical device is located inside or outside the target region and for setting the first or second state, accordingly.

Although in above described embodiments the first and the second state of the medical device are realized by providing mechanical or electrical means for locking and unlocking the part of the medical device that should affect the subject, in another embodiment the first state and the second state can be realized as virtual first state and virtual second state. The virtual first state is realized through software means preventing the affecting of the subject by the medical device when a trigger signal is provided to the medical device. The second virtual state is realized through software means allowing the affecting of the subject through the medical device when the trigger signal is provided. In an embodiment the first and second virtual states can be realized as part of the device control unit, wherein the device control unit only sends the trigger signal to the medical device when the second virtual state is set.

Although in above described embodiments an image providing unit is contemplated for providing an image of the medical device, wherein the device location determination unit is adapted to determine the location of the medical device based on the provided image, in another embodiment the device location determination unit can be adapted to determine the location of the medical device based on an optical shape sensing system provided on the medical device, or an electromagnetic tracking system.

Although in above described embodiments in the first state, i.e. the safety state, the medical device was configured to not affect the subject when the trigger signal is provided, in another embodiment the medical device can comprise an override mode, wherein the device control unit sets the medical device to the override mode based on an input provided by a user, i.e. a medical practitioner. The override mode configures the medical device such that in the first state the medical device affects the subject based on the provision of the trigger signal. In this embodiment a signal is further provided by the device control unit comprising an indication that the medical device is set to override mode. The signal can be used for providing an alarm for notifying the user or for providing a protocol notifying that the override mode was used, i.e. that the medical device affected the subject outside the predetermined plan. This embodiment allows the user flexibility to deviate from a predetermined treatment plan if certain circumstances require such a deviation. Preferably, in this embodiment, if a danger region is provided by the target region providing unit, the medical device cannot be set into the override mode if the device control unit determined that the medical device is in the danger region. Thus, also in this case it can be ensured that regions in which it is very important to not affect the subject cannot be affected.

Although in the above described embodiments the target region providing unit has only provided one target region in which, for instance, a biopsy should be taken, in other embodiments the target region providing unit can be adapted to provide more than one, preferably, a plurality, of target regions. The device control unit can then be adapted to set the medical device to the second state, for instance, the armed state, if the medical device is located in any of these target regions.

Although in above described embodiments the medical device is a biopsy gun, also other medical devices can be contemplated that are adapted to be set in a first state, i.e. unarmed state, and a second state, i.e. armed state. In another preferred embodiment the medical device is a brachytherapy applicator for setting radioactive seeds at predetermined locations within a patient when a trigger signal is provided.

Moreover, in a further exemplary embodiment the medical device can also be a stent or balloon applicator. For instance, in cardiovascular or neurovascular applications a stent or a balloon, preferably a drug coated balloon, should be applied from healthy to healthy tissue such that it bridges a lesion in the vascular system of a patient. To achieve this goal, the distal end of the stent or balloon must be placed in a specific landing zone such that, when opening the stent or balloon, the distal end of the stent or balloon is in healthy tissue and the proximal end of the stent or balloon also reaches again into healthy tissue. Since the length of the stent or balloon is limited, it is important that the distal end is placed within the landing zone very accurately. When the medical device is a stent or balloon, preferably a drug coated balloon, the target region providing unit can be adapted to provide as target region the landing zone of the distal end of the stent or balloon, wherein the device control unit is then adapted to set the stent or balloon applicator from a first state in which the patient cannot be affected by opening and/or placing the stent or balloon to a second state in which the applicator can affect the patient by opening and/or placing the stent or balloon, when the device control unit determines that the distal end of the stent or balloon is in the landing zone. Preferably, in such an application the first state can comprise a first stage and a second stage, wherein in the first stage the applicator is not able to open or place a stent or balloon, but can only be navigated to the target region, i.e. is able to be moved, for instance, by a medical robot or a user, from one position to another position, and wherein in the second stage the applicator is able to partially open the stent or balloon but is not able to place the stent or balloon, i.e. is not able to affect the patient with the stent or balloon. Preferably, in this case the device control unit is adapted to set the applicator in the second stage of the first state when the distal end of the stent or balloon reaches the landing zone. A surgeon can then partially open the stent or balloon by providing a change signal, but the surgeon cannot yet place the stent or balloon. After the stent or balloon has been partly opened or upon a further request signal from the surgeon or robot, the device control unit can then be adapted to check whether the partially opened stent or balloon is still in the determined landing zone, i.e. target region, and if this is the case, set the applicator to the second state, such that when the surgeon or robot provides the trigger signal the stent or balloon is completely opened and placed. Additionally or alternatively, the target region providing unit can also provide a sub-region of the target region such that the medical control unit can set the applicator to the second stage upon reaching the target region and into the second state upon reaching the sub-region.

In another exemplary embodiment the medical device can be an electrosurgical device, preferably an electrosurgical knife. In such an embodiment, in the first state the electrosurgical device can be in a resting state in which no electrical power is provided to the electrosurgical device and in the second state the electrosurgical device can be in an active state in which electrical power is applied to the electrosurgical device such that a surgeon can, by providing a trigger signal, apply a high-frequency electrical current to the tissue of the patient. This allows the surgeon to navigate the electrosurgical device safely into the target region in which the electrical current should be applied before the electrosurgical device is set to the second state. Preferably, the electrosurgical device is used during a brain surgery. During brain surgery it is crucially important to only affect the brain of the patient, for instance, by removing tissue in the brain of the patient, in a predetermined area, like along tumor tissue in the brain. In such an application the target region can be determined, for instance, based on an MR image of the brain of the patient and the location of the electrosurgical device can be provided based on a localization system, like an electromagnetic localization system, registered with the MR image of the brain of the patient. In this exemplary embodiment the device control unit can be adapted to provide an electrical current to the electrosurgical device, i.e. to set the electrosurgical device in the second state, only if the electrosurgical device, in particular the tip of the electrosurgical device, is located in the predetermined brain region, such that the electrosurgical device only provides a current to the tissue based on a trigger signal when it is ensured that no tissue other than the predetermined tissue is affected. This embodiment allows to make brain surgery more reliably and safer for the patient. Another preferred application of this embodiment is in heart surgery, preferably, for ablating heart tissue for treating arrhythmias. Also in this application it is advantageous to ensure, based on the principles laid out above, that only heart tissue in a predetermined region can be affected by the electrosurgical device when a trigger signal is provided to the device.

In a further embodiment the medical device can be an interventional device that is adapted for being used during a lung biopsy. Preferably, in this case the interventional device is a catheter-like device that can be navigated through the bronchial airways of the lung of a patient to a target region. Moreover, the interventional device can be provided with a biopsy needle, wherein in the second state the biopsy needle can be stabbed into tissue of the patient, for instance, a tumor, based on the trigger signal. Preferably, the device control unit is adapted to set the interventional device into the second state further based on an orientation of the medical device. In particular, the device control unit can further be adapted to check in addition to the location of the interventional device also an orientation of the device, wherein if the interventional device is within a target region and also in a predetermined target orientation, the interventional device is set to the second state. This allows to ensure that the needle is only used in a region and an orientation that is safe for the patient.

In another embodiment the medical device can be a medical drill or a screwdriver, preferably adapted for spine surgery, wherein in the first state the medical drill or screwdriver are not able to rotate the drill bit or the screw, respectively. In spinal surgery screws have to be inserted into the spine, wherein it is important not to damage nerves running through the spine to avoid serious side-effects. In such an embodiment the device control unit can be adapted to set the medical drill or screwdriver in the first state if the device control unit determines that the position of the medical drill or screwdriver differs from a target region or is within a predetermined danger region. Thus, it can be ensured that the drill or screwdriver is not able to damage the spine in possibly dangerous places, i.e. near important nerves.

Also other applications of the invention can be contemplated. For instance, the medical device can also be an injection device for injecting an anesthetic into a nerve region under image guidance for applying a regional anesthesia. In such cases it is important that the anesthetic is injected near the nerve but at the same time that blood vessels are not damaged and that the anesthetic is not injected into a blood vessel or into the nerve itself. In this case the device control unit can be adapted to set the injection needle into a second state in which it is able to inject the anesthetic, when it is determined, for instance, based on an ultrasound image, that the tip of the needle is in a target region near the nerve. Further, the device control unit can be adapted to set the injection needle into the first state, in which it is not able to inject the anesthetic, if the device control unit determines that the tip of the needle has left the target zone, or is near a predetermined danger region, for instance, around a blood vessel or the nerve itself.

Further, the medical device can be an arterial or atherectomy device, a thrombectomy device, a laser ablation device, or a cryotherapy device.

Figure 2:
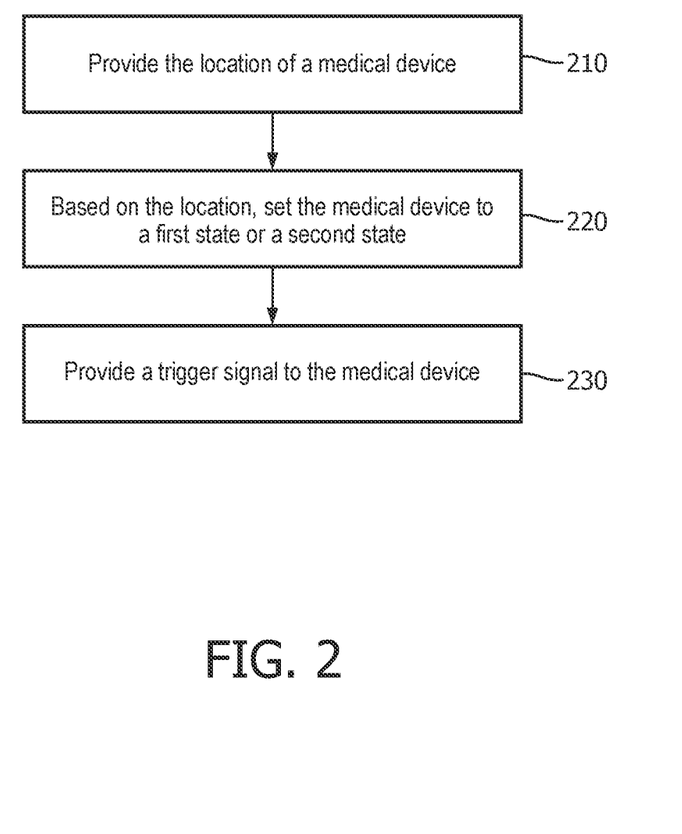
FIG. 2 shows a flowchart exemplarily illustrating an embodiment of a method for operating the system for affecting a subject.

In the following an embodiment of a method for operating the above described system will be exemplarily described with reference to a flowchart shown in FIG. 2.

In step 210 the location of the medical device is provided by the device location providing unit. The location of the medical device is, for instance, provided based on an image of an image providing unit as described above.

Based on the provided location of the medical device the medical device is set to the first state or the second state in step 220. In particular, a target region is provided, wherein the medical device is set to the first state when it is determined that the medical device is outside of the target region, and to the second state when it is determined that the medical device is within the target region.

In step 230 a trigger signal is provided, wherein the trigger signal is preferably provided when the medical device is in the second state.

A main element of the invention of the system for affecting a subject is that information is transferred between a device location providing unit, i.e. an image providing unit, and a medical device like a biopsy gun. This information can be data such as a number/identifier of a biopsy being taken or the location of the medical device. In particular, a previously defined treatment plan, i.e. a biopsy taking plan, is executed such that only when the medical device, i.e. the biopsy needle tip, is sufficiently close to a preplanned location the medical device is set into the armed state and only in this armed state the person executing the medical treatment procedure can trigger the medical device, i.e. take the biopsy. The medical device is considered as being sufficiently close to a preplanned location if the location of the medical device deviates by less than a certain predetermined amount from the preplanned location, wherein this predetermined deviation around the planned location defines the target region. The predetermined deviation, and hence the target region, can be determined based on the characteristics and/or structure of the tissue around the preplanned location.

The invention recognizes that during the navigation of a medical treatment, in particular a biopsy gun, even under image guidance deviations from an intended predefined navigation or treatment plan cannot be ruled out completely. Thus, using the principles of the invention as explained above has the advantage of ensuring that a treatment, i.e. an effect on the patient, is only provided in an intended area, as defined, for instance, through a pre-procedure MRI image. Further, the determination of the location of the medical device may help to improve a proper reconstruction of a tumor when, for instance, multiple interact/3D biopsies are taken. Moreover, the system of the invention allows to safely automate the navigation and control of the medical device, for instance, during a biopsy taking process.

Other variations to the disclosed embodiments can be understood and effected by those skilled in the art and practicing the planned invention from the study of the drawings, the disclosure and the appendant claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutual different dependent claims does not indicate that a combination of these measures cannot be used to advantage.

Procedures like the providing of the location of the medical device or the setting of the first or the second state performed by one or several units or devices can be performed by any other number of units or devices. These procedures and/or the operation of the system can be implemented as program code means of a computer program and/or as dedicated hardware.

A computer program may be stored/distributed in a suitable medium, such as an optical storage medium or a solid state medium, supplied together with or as part of other hardware, but may also be distributed in other forms, such as via the Internet or other wired or wireless telecommunication systems.

Any reference signs in the claims should not be construed as limiting the scope.

The invention refers to a system for affecting a subject and a method for operating the system comprising a medical device like a biopsy gun set in a first state in which it is not able to affect the subject based on a trigger signal or in a second state in which it is able to affect the subject based on the trigger signal, wherein the state is set based on a provided location of the medical device, i.e., for instance, is set based on the distance of the medical device to a target region. The location of the medical device is provided by a location providing unit comprising, for instance, an imaging unit like an ultrasound system. Thus, unintended, possible dangerous injuries of the patient are prevented and the safety of the patient during the interventional procedure is increased.

The invention claimed is:

1. A system for affecting a subject, the system comprising:
a medical device configured to affect the subject, the medical device configured to be in a first state, in which the medical device is not able to affect the subject in response to a trigger signal, or a second state, in which the medical device is able to affect the subject in response to the trigger signal, wherein, in the first state, the medical device is further configured to be in a first stage of the first state, in which the medical device is not able to change a physical state of the medical device, or a second stage of the first state, in which the medical device is able to change the physical state of the medical device;
an imaging system configured to provide an image that includes the medical device and a target region in the subject for the medical device to affect the subject; and
at least one processor configured to:
receive, from the imaging system, the image,
detect the medical device within the image,
determine a location of the detected medical device within the image and a location of the target region within the image,
determine, from the image, a relation of the location of the medical device within the image to the location of the target region within the image,
set the medical device to the first state or the second state based on the determined relation of the location of the medical device to the location of the target region, and
if the medical device is set to the first state, set the medical device to the first stage of the first state or second stage of the first state based on the determined relation of the location of the medical device to the location of the target region.

2. The system as defined in claim 1, wherein the at least one processor is further configured to:
set the medical device to the first state, if the location of the medical device is outside the target region and to the second state, if the location of the medical device is within the target region.

3. The system as defined in claim 2, wherein the medical device comprises a plurality of second states, and, in each of the second states, the medical device is able to affect the subject differently in response to the trigger signal, and the at least one processor is further configured to:
determine, based on characteristics of the target region, a state of the plurality of second states, and
set the medical device to the determined state, if the provided location of the medical device is within the target region.

4. The system as defined in claim 1, wherein the image that includes the medical device is provided by an ultrasound device or an X-ray device.

5. The system as defined in claim 1, wherein the medical device is a biopsy gun or a brachytherapy applicator, and the first state is an unarmed state of the biopsy gun or the brachytherapy applicator and the second state is an armed state of the biopsy gun or the brachytherapy applicator.

6. The system as defined in claim 1, wherein the medical device is a stent applicator comprising a stent or a balloon applicator comprising a balloon, wherein in the first stage of the first state, the stent applicator or the balloon applicator is not able to change a physical state of the stent or balloon, respectively, and in the second stage of the first state, the stent applicator or the balloon applicator is able to change the physical state of the stent or the balloon, respectively, and wherein in the second state the stent applicator or the balloon applicator is able to apply the stent or the balloon, respectively, to the subject based on the trigger signal.

7. The system as defined in claim 1, wherein the medical device is an electrosurgical device, and wherein the first state is a resting state of the electrosurgical device and the second state is an active state of the electrosurgical device.

8. The system as defined in claim 1, further comprising a medical robot configured to:
navigate the medical device, and
provide the trigger signal to the medical device when the medical robot determines, based on the location of the medical device, that the medical device is at a predetermined location.

9. The system as defined in claim 1, wherein the at least one processor is further configured to:
determine an orientation of the detected medical device within the image, and
set the medical device to the first state or the second state based further on the orientation of the medical device within the image.

10. The system as defined in claim 1, wherein the at least one processor is further configured to:
determine a distance from the location of the medical device to the location of the target region within the image; and
set the medical device to the first state or the second state based on the determined distance.

11. The system as defined in claim 10, wherein the at least one processor is further configured to:
determine the target region to include a deviation amount around a planned location to affect the subject, wherein the deviation amount is determined based on a characteristic of tissue around the planned location; and
set the medical device to the second state based on the determined distance being less than the deviation amount around the planned location.

12. The system as defined in claim 1, wherein the at least one processor is further configured to:
adjust imaging settings of the imaging system to a first setting if the medical device is set to the first state or to a second setting if the medical device is set to the second state.

13. A method for operating a system to affect a subject, the method comprising:
receiving, from an imaging system, an image that includes a medical device and a target region in the subject for the medical device to affect the subject;
detecting the medical device within the image;
determining a location of the detected medical device within the image;
determining, from the image, a relation of the location of the medical device within the image to the location of the target region within the image,
controlling the medical device, including setting the medical device to a first state, in which the medical device is not able to affect the subject in response to a trigger signal, or to a second state, in which the medical device is able to affect the subject in response to the trigger signal, based on relation of the location of the medical device to the location of the target region, and
if the medical device is set to the first state, controlling the medical device, including setting the medical device to a first stage of the first state, in which the medical device is not able to change a physical state of the medical device, or a second stage of the first state, in which the medical device is able to change the physical state of the medical device, based on relation of the location of the medical device to the location of the target region.

14. The method as defined in claim 13, further comprising:
    determining an orientation of the detected medical device within the image; and
    setting the medical device to the first state or the second state based further on the orientation of the medical device within the image.

15. The method as defined in claim 13, further comprising:
    determining a distance from the location of the medical device to the location of the target region within the received image; and
    setting the medical device to the first state or the second state based on the determined distance.

16. The method as defined in claim 15, further comprising:
    determining the target region to include a deviation amount around a planned location to affect the subject, wherein the deviation amount is determined based on a characteristic of tissue around the planned location; and
    setting the medical device to the second state based on the determined distance being less than the deviation amount around the planned location.

17. A non-transitory computer readable medium having stored therein a computer program for operating a system for affecting a subject, the computer program comprising instructions which, when executed by a processor, cause the processor to:
    receive, from an imaging system, an image that includes a medical device and a target region in the subject for the medical device to affect the subject;
    detect the medical device within the image,
    determine a location of the detected medical device within the image and a location of the target region within the image;
    determine, from the image, a relation of the location of the medical device within the image to the location of the target region within the image,
    set the medical device to a first state, in which the medical device is not able to affect the subject in response to a trigger signal, or to a second state, in which the medical device is able to affect the subject in response to the trigger signal, based on relation of the location of the medical device to the location of the target region within the image, and
    if the medical device is set to the first state, set the medical device to a first stage of the first state, in which the medical device is not able to change a physical state of the medical device, or a second stage of the first state, in which the medical device is able to change the physical state of the medical device, based on relation of the location of the medical device to the location of the target region.

18. The non-transitory computer readable medium as defined in claim 17, wherein the instructions, when executed by the processor, further cause the processor to:
    determine an orientation of the detected medical device within the image; and
    set the medical device to the first state or the second state based further on the orientation of the medical device within the image.

19. The non-transitory computer readable medium as defined in claim 17, wherein the instructions, when executed by the processor, further cause the processor to:
    determine a distance from the location of the medical device to the location of the target region within the received image; and
    set the medical device to the first state or the second state based on the determined distance.

20. The non-transitory computer readable medium as defined in claim 19, wherein the instructions, when executed by the processor, further cause the processor to:
    determine the target region to include a deviation amount around a planned location to affect the subject, wherein the deviation amount is determined based on a characteristic of tissue around the planned location; and
    set the medical device to the second state based on the determined distance being less than the deviation amount around the planned location.

* * * * *